(12) United States Patent
Ueno et al.

(10) Patent No.: US 7,381,839 B2
(45) Date of Patent: Jun. 3, 2008

(54) METHOD FOR PRODUCING ACRYLIC ACID

(75) Inventors: Koji Ueno, Himeji (JP); Yoshitake Ishii, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 11/655,063

(22) Filed: Jan. 19, 2007

(65) Prior Publication Data

US 2007/0173665 A1 Jul. 26, 2007

(30) Foreign Application Priority Data

Jan. 20, 2006 (JP) .............................. 2006-013207

(51) Int. Cl.
*C07C 51/42* (2006.01)
*C07C 57/02* (2006.01)

(52) U.S. Cl. ...................................... 562/600; 562/598

(58) Field of Classification Search ...................... None
See application file for complete search history.

(56) References Cited

U.S. PATENT DOCUMENTS

| | | | |
|---|---|---|---|
| 5,817,865 A | 10/1998 | Machhammer et al. | |
| 6,482,981 B2 | 11/2002 | Ueno et al. | |
| 7,129,376 B2 | 10/2006 | Hammon et al. | |
| 2002/0165410 A1 | 11/2002 | Aichinger et al. | |
| 2004/0097756 A1* | 5/2004 | Thiel et al. ................ | 562/600 |
| 2004/0133015 A1 | 7/2004 | Hammon et al. | |

FOREIGN PATENT DOCUMENTS

| | | |
|---|---|---|
| EP | 1 097 741 | 5/2001 |
| EP | 1 361 203 | 11/2003 |
| JP | 53-41637 | 11/1978 |
| JP | 9-227445 | 9/1997 |
| JP | 2001-129388 | 5/2001 |
| JP | 2001-199931 | 7/2001 |
| JP | 2004-528370 | 9/2004 |
| JP | 2004-528371 | 9/2004 |
| JP | 2005-15478 | 1/2005 |

* cited by examiner

*Primary Examiner*—Paul A Zucker
(74) *Attorney, Agent, or Firm*—Wenderoth, Lind & Ponack, L.L.P.

(57) ABSTRACT

The objective of the present invention is to provide method for acrylic acid in which a generation of polymerized substance is prevented while acrylic acid is stored in a storage tank. A method of the present invention for producing acrylic acid, comprising storing acrylic acid in a storage tank, wherein a process liquid containing 50 mass % or more of acrylic acid is subjected to at least one filtering operation at 15 to 70° C. when the process liquid is supplied to the storage tank.

5 Claims, No Drawings

METHOD FOR PRODUCING ACRYLIC ACID

TECHNICAL FIELD

The present invention relates to a method for producing acrylic acid.

BACKGROUND ART

Acrylic acid is a very easily polymerized substance, and a variety of methods are used to prevent the polymerization during the production of acrylic acid. Most of them are associated with polymerization prevention by the addition of a stabilizer. In each step of the production, the addition of a stabilizer can prevent the polymerization to the extent that no hindrances are caused during the operation of apparatuses. However, the polymerization cannot completely be prevented, thereby causing a trace amount of polymerized substances to be present in the acrylic acid. The presence of these polymerized substances is a factor of causing further polymerization even if a sufficient amount of a stabilizer is present. That is, such a slight amount of polymer causes the polymerization of acrylic acid while acrylic acid is stored.

Hence, in the production of acrylic acid, it is important to remove this polymerized substance. Some methods of removing the polymerized substance are disclosed in, for example, Published Japanese Translation of PCT International Publication Nos. 2004-528370, 2004-528371 and Japanese Unexamined Patent Publication No. 2001-129388. For example, in the publication No. 2004-528370, crude acrylic acid melt to be supplied to a step of crystallization is filtered through a filter to remove an adhesive polymer that does not have a high molecular weight. In the publication No. 2004-528371, filtration through a filter is carried out to remove an adhesive polymer just before a mother liquor or suspended crystal of suspension crystallization of acrylic acid is re-crystallized. In the publication No. 2001-129388, filtration through a strainer or the like is carried out in a circular pathway outside of a distillation column, a fractionation column and the like, to remove solid impurities.

However, as the methods described in the publications Nos. 2004-528370, 2004-528371 and 2001-129388, even if polymerized substances are removed in the production process of acrylic acid, the increase of polymerized substances in purified acrylic acid is seen with a time lapse, which causes the problem of decreasing the purity of the purified acrylic acid. Moreover, the method of carrying out filtration prior to purification as described above sometimes stores crude acrylic acid in a storage tank prior to purification. In this case, the amount of polymerized substance is increased during the storage. As a result, there is the problem of frequent clogging of the filter caused by the polymerized substance when filtration processing is performed prior to the purification step.

DISCLOSURE OF THE INVENTION

Under the above situations, an object of the present invention is to provide a production method of acrylic acid in which the generation of polymerized substances is prevented during the storage of acrylic acid in a storage tank.

The present inventors have diligently studied and found that dissolved polymerized substances cannot be removed during the supply of acrylic acid solution to the step of crystallization even though ordinary filtration processing is carried out, and thus polymerized substances deposit while the acrylic acid is purified in the crystallization step, and further new polymerized substances are generated even in the crystallization step. As a result, it was found that there is a small amount of polymerized substances in the purified acrylic acid. Furthermore, it was found that, even in the case of purification in the distillation step, the purified acrylic acid is generally obtained from a upper portion, that is column top side, over the raw material supplying portion of a distillation column, but even in this case, polymerized substances of acrylic acid generated in a condenser portion or the like may be mixed into the purified acrylic acid.

As described above, when polymerized substances are present in acrylic acid to be supplied to a storage tank, the polymerized substances further facilitate the generation of polymerized substances. Thus, the present inventors have further diligently studied and found that the filtration of crude acrylic acid and/or purified acrylic acid at the time of its storage in a storage tank can remove the polymerized substances in acrylic acid to be supplied to the storage tank, and further can sufficiently deposit and sufficiently remove the polymerized substances dissolved in the acrylic acid at a predetermined temperature. Thus, the present inventors have completed the present invention.

A method of the present invention for producing acrylic acid, comprising:

storing acrylic acid in a storage tank, wherein a process liquid containing 50 mass % or more of acrylic acid is subjected to at least one filtering operation at 15 to 70° C. when the process liquid is supplied to the storage tank.

DETAILED DESCRIPTION OF THE INVENTION

According to the present invention, the generation of polymerized substances can be prevented at the time of storage of acrylic acid in a storage tank in a step of producing acrylic acid. When acrylic acid is filtered prior to a step of purification at the time of supply to a storage tank, the generation of polymerized substances can be prevented in the storage tank, thereby, for example, the frequency of changing filters used in filtration prior to the step of purification can be reduced. Further, the amount of polymerized substances mixed in the step of purification can be reduced, thereby the production efficiency is improved. Moreover, when acrylic acid after the step of purification is filtered at the time of supply to a storage tank, acrylic acid to be the final product can be stably stored for a long period of time. Thus, acrylic acid that rarely tends to decrease in purity and thus acrylic acid with high stability can be provided as a product by the present invention.

A method of the present invention for producing acrylic acid, comprising:

storing acrylic acid in a storage tank, wherein a process liquid containing 50 mass % or more of acrylic acid is subjected to at least one filtering operation at 15 to 70° C. when the process liquid is supplied to the storage tank.

In the production of acrylic acid, crude acrylic acid to be supplied to the step of purification may be stored in a storage tank, or acrylic acid subsequent to purification may be stored in a storage tank to provide for shipping or transport. The present invention relates to a method for producing acrylic acid including such a step of storing acrylic acid in a storage tank.

A producing method of the present invention may only include a step of storing the process liquid in the storage tank, and does not depend on other kinds of producing steps of acrylic acid, but preferably contains the following steps (a) to (c):

(a) obtaining an acrylic acid-containing gas by a vapor-phase catalytic oxidation reaction from an acrylic acid raw material;

(b) obtaining a crude acrylic acid by at least one of absorbing or condensing the acrylic acid-containing gas; and (c) purifying acrylic acid from the crude acrylic acid by at least one of distillation or crystallization.

In the step (a), an acrylic acid-containing gas is produced by catalytic vapor phase oxidation reaction. The reaction is well-known to the person skilled in the art, and the person skilled in the art can produced an acrylic acid-containing gas by the reaction according to conventional method.

In the step (b), a crude acrylic acid is obtained by at least one of absorbing the acrylic acid-containing gas produced by catalytic vapor phase oxidation reaction in a solvent or condensing the acrylic acid-containing gas. The method for obtaining the aforementioned crude acrylic acid is well-known and described in, for example, Japanese Publication of Unexamined Patent Application 2005-15478, and the like.

Solvents used for absorbing the acrylic acid-containing gas include water; water containing organic acid; inert and hydrophobic organic liquids with high boiling points such as diphenyl ether, diphenyl, and the like; and these mixtures. Among these, water; and the mixed solvent of diphenyl ether and diphenyl are preferable.

Components other than acrylic acid in the crude acrylic acid include by-products of catalytic vapor phase oxidation reaction, such as water, acetic acid, maleic acid, aldehydes, acrylic acid polymers, and the like, and solvents absorbing the above-mentioned acrylic acid-containing gas, and the like.

The crude acrylic acid may contain a polymerization inhibitor, a stabilizer, and the like. The acrylic acid polymer is still formed even if a polymerization inhibitor, a stabilizer, and the like are contained.

In the step (c), acrylic acid is purified from the crude acrylic acid by at least one of distillation or crystallization. These purification methods are well-known and described in, for example, Japanese Publication of Unexamined Patent Application Nos. 09-227445, No. 2005-15478, and the like.

In the present invention, a process liquid containing 50 mass % of acrylic acid is treated. The process liquid is not particularly limited as long as liquid in the step of producing acrylic acid and it contains 50 mass % or more of acrylic acid. The amount of acrylic acid contained in the process liquid is preferably 70 mass % or more, more preferably 80 mass % or more, still more preferably 90 mass % or more. A process liquid containing acrylic acid is as low as less than 50 mass % has an extremely small amount of polymerized substances during storage in a storage tank, thereby hardly posing the problem of the generation of polymerized substances. Therefore, the present invention has a sufficient effect on a process liquid containing 50 mass % or more of acrylic acid.

The examples of the process liquid include the acrylic acid solution obtained by condensation of an acrylic acid-containing gas obtained by a vapor-phase catalytic oxidation reaction, the acrylic acid solution obtained by absorbing the acrylic acid-containing gas in a solvent, and the like. The process liquid containing 50 mass % of acrylic acid is obtained from the above acrylic acid solution by conventional method such as controlling the amount of the solvent for absorbing and condensing the solution. The process liquid may be the purified acrylic acid having completed a step of purification, and the like. More specifically, the examples include a column bottom flow or column side flow of an absorption column, a condensation column, a distillation column or the like, and further acrylic acid obtained by purification of the column bottom flow or column side flow in the step of distillation and/or crystallization, and the like. The process liquid is preferably purified acrylic acid, and its preferred examples include acrylic acid obtained by purification of acrylic acid obtained as a column bottom flow and/or column side flow of the absorption column, the condensation column and/or the distillation column in the step of distillation and/or crystallization.

The method of the present invention is particularly useful in case that acrylic acid is purified by crystallization and stored after the purification. The crude acrylic acid before purification can contain relatively great deal of water, and acrylic acid polymer is highly soluble in water. Therefore, acrylic acid polymer in crude acrylic acid cannot be adequately filtered out before crystallization in some cases, since acrylic acid polymer is solved by water. However, water can be easily separated off in crystallization process to reduce an amount of water. Accordingly, acrylic acid polymer is easy to be separated out and filtered out by filtrating melted and purified acrylic acid in specific condition after crystallization process and before storing process by the present invention, since an amount of water in acrylic acid is decreased. As a result, the deposition of polymer during the storing process due to the small amount of polymer is decreased. Such an effect is exerted in case that an amount of water in crude acrylic acid before crystallizing process is large and the amount of water after crystallizing process is small. Therefore, the method of the present invention is particularly useful in case that water is contained in acrylic acid to be supplied to crystallization process in an amount of 0.5 mass % or more, further 1 mass % or more, or still further 1.5 mass % or more, and water is contained in purified acrylic acid in an amount of 0.3% or less, further 0.2% or less, or still further 0.1% or less.

In the present invention, the process liquid is stored in a storage tank, and the process liquid is subjected to at least one filtering operation at 15 to 70° C. when the process liquid is supplied to the storage tank.

The storage tank refers to a vessel capable of accommodating the liquid for a pre-established period of time, and the examples include a polyethylene tank, a drum, a container, a tank-like construct, a tank lorry, tanker, and the like.

Examples of the step of storing the process liquid in the storage tank include a step of storing the acrylic acid solution in the storage tank prior to the step of purification, a step of storing the acrylic acid in the storage tank subsequent to the step of purification, and the like.

In these steps, the storage tank is placed, in terms of the location among the steps, for example, between a absorption column, a condensation column and/or a distillation column and a fractionation column and/or a crystallization column, or downstream of a fractionation column and the like and/or a crystallization column.

A residence time of the process liquid in the storage tank is, although depending on a temperature of the process liquid during storage, preferably 0.5 hour or more, more preferably one hour or more, still preferably two hours or more. In these cases, the present invention is particularly useful.

In the present invention, the specialized filtrating operation of the process liquid at the time of its supply to the storage tank is carried out. In the conventional methods, such a filtrating operation is not carried out. By the filtration at the time of supply of the process liquid to the storage tank prior to a step of purification, the generation of polymerized substances during the storage can be prevented. As a result, for example, the frequency of changes of filters used in filtration subsequent to the storage and prior to the step of purification can be decreased. In addition, the filtration can decrease the amount of polymerized substances mixed during the step of purification, and thus can improve production efficiency. Alternatively, in case that the filtration is carried out at the time of supply of the process liquid to the storage tank subsequent to a step of purification, the process liquid can be stably stored for a long period of time. In particular, the process liquid after step of purification is acrylic acid to be the final product, so it is extremely important to be able to stably store the process liquid for a long period of time.

"Carrying out a filtrating operation of the process liquid when the process liquid is supplied to the storage tank" refers to "carrying out a filtrating operation of the process liquid when the process liquid is substantially directly transported the storage tank." That is, in the present invention, facilities such as an absorption column and distillation column are not disposed between the filter for filtration and the storage tank. The filtrating operation of the process liquid is carried out by the filter placed on transport facilities such as a liquid transport line and the like directly communicated with the storage tank.

The filtrating operation is carried out at 15 to 70° C. The reason why the temperature of the process liquid for filtration is set at 70° C. or less is that a temperature of 70° C. or less makes low the solubility of polymerized substances of acrylic acid in the process liquid and thus the polymerized substances is deposited. Additionally, this is because the production of new polymerized substances is prevented though acrylic acid has high polymerization reactivity. On the other hand, since the melting point of acrylic acid is about 13° C., the filtrating operation is carried out at 15° C. or higher from the viewpoint of the prevention of a decrease in filtration efficiency on account of the crystal deposition of acrylic acid. The temperature of the filtrating operation is preferably from 15 to 60° C., more preferably from 15 to 50° C. When the temperature of the process liquid to be supplied to the storage tank is higher than 70° C., the liquid may be cooled by a heat exchanger or the like.

In a filtrating operation, the linear velocity of the process liquid is preferably 5 m/s or less, more preferably from 0.0005 to 2 m/s, most preferably from 0.001 to 1.0 m/s. When the linear velocity exceeds 5 m/s, the possibility of passing deposited polymerized substances through the filter is raised. The linear velocity in the present invention can be evaluated by dividing the amount of solution passing through the filter by the filtration area of the filter.

The filter is not particularly limited, and a normally used filter can be utilized as the filter. The examples include filters of materials such as a glass fiber, a metal fiber, polyester, fluorocarbon, polyethylene, polypropylene, polyamide, polystyrene, cellulose, cellulose acetate, unwoven cloth, woven cloth, filter paper, and ceramics. Among them, filters made of a stainless metal fiber, ceramics, and polypropylene are preferable.

The pore diameter of the filter may be a size that can filtrate deposited polymerized substances of acrylic acid, and is preferably in the range of 0.01 to 1000 µm, more preferably from 0.1 to 500 µm, further preferably from 0.1 to 100 µm.

The filter may be placed in a plurality of stages, and the filters to be placed may be the same kind or a different kind each other. In terms of prolonging the life of the filtration portion, a plurality of kinds of filters may be placed in series in the order of from a large mesh filter to a small mesh filter. For example, the first stage has 100 to 1000 µm, more preferably has 120 to 1000 µm; the second stage or later stage has 0.1 to 100 µm, more preferably 0.5 to 100 µm, still more preferably 1 to 80 µm. When a bypass is placed to provide for filter change or the like, the filter arrangement, configuration and material in the bypass are preferably the same as those of the main pass.

As the filter is used, absorption of polymerized substances of acrylic acid causes clogging. However, the polymerized substances of acrylic acid can be easily removed by carrying out reverse cleaning and/or water cleaning, and alkali cleaning in that order. Further cleaning with water enables reuse of the filter material. Since liquid of water cleaning upon the first water cleaning contains acrylic acid, the liquid may be returned to the step of producing acrylic acid, such as absorbing process, to recover the acrylic acid.

A filtrating operation at the time of the supply of the process liquid to the storage tank is preferably carried out in all of the steps of storage when a plurality step of the process liquid being stored in a plurality of storage tanks is present in the producing step.

When the liquid within the storage tank is circulated by using a pump or the like in order to render the liquid within the storage tank to be homogeneous, a filtrating operation may be carried out also in the circulating pathway.

Moreover, when the process liquid after the step of purification is transferred from a storage tank to another storage tank, such as when the liquid is transferred from a tank-like construct to a tank truck, tanker, or the like, filtration may also be carried out in a manner similar to the method as described above.

EXAMPLES

The present invention will be described by Examples and Comparative Examples hereinafter. The present invention, however, should not be limited by these Examples.

Reference Example 1

Preparation of an Acrylic Acid Solution

An acrylic acid-containing gas was obtained by a vapor-phase catalytic oxidation reaction of propylene in a similar manner to Example 1 of Japanese Unexamined Patent Publication No. 2005-15478. The gas was contacted with an aqueous solution for absorption in an absorption column to obtain an acrylic acid solution from the column bottom of the absorption column. The acrylic acid had a composition of 90.0 mass % of acrylic acid, 3.2 mass % of water, 1.9 mass % of acetic acid, 0.6 mass % of maleic acid, 1.5 mass % of an acrylic acid dimmer, 0.4 mass % of aldehydes, 0.1 mass % of hydroquinone, and 2.3 mass % of other impurities. At this time, the temperature of the absorption column bottom and thus the temperature of the acrylic acid solution taken out of the absorption column were 91° C.

Example 1

The acrylic acid solution obtained in Reference Example 1 was cooled to 70° C. by using a heat exchanger, and then supplied to a storage tank through a line in which a cartridge filter made of polypropylene with a pore diameter of 50 µm was placed. Hereinafter, the filter is referred to as Filter A.

The acrylic acid solution was continuously taken out of the storage tank in such a way that the residence time of the acrylic acid solution in the storage tank was one hour. At this time, the linear velocity of the acrylic acid solution at Filter A portion was 0.1 m/s. Then, the acrylic acid solution was supplied to a step of purification.

In a line through which the acrylic acid solution was taken out of the storage tank, a cartridge filter made of polypropylene with a pore diameter of 50 μm was placed. Hereinafter, the filter is referred to as Filter B. The operation was continuously performed for one month. As a result, the increase of pressure drop was not seen at filter B, and also a deposit such as polymer was not seen on the surface of Filter B taken out. The increase of pressure drop was not seen also on Filter A; however, a deposited polymer was on the surface of Filter A taken out.

Comparative Example 1

An operation similar manner to Example 1 was carried out except that Filter A was not placed. After a continuous operation was carried out for 3 days, the pressure drop was increased at Filter B, so that it became difficult to take the acrylic acid solution out of the storage tank. A deposited polymer was on the surface of Filter B taken out, and most of the filter pores were clogged.

Comparative Example 2

An operation similar manner to Example 1 was carried out except that the acrylic acid solution taken out of the absorption column was cooled to 80° C. by using the heat exchanger. After a continuous operation was carried out for 4 days, the pressure drop was increased at Filter B, so that it was difficult to take the acrylic acid solution out of the storage tank. A deposited polymer was on the surface of Filter B taken out, and most of the filter pores were clogged. In addition, the increase of the pressure drop was not seen at Filter A.

Example 2

An acrylic acid solution was obtained in a similar manner to the case of Reference Example 1, and directly supplied to an apparatus of crystallization without being passed through a storage tank, and then purified four times in a step of dynamic crystallization. The dynamic crystallization was performed in an apparatus of crystallization purification in accordance with the crystallizing apparatus described in Japanese Examined Patent Publication No. 53-41637. In other words, the apparatus includes a metal tube having a length of 6 m and an inner diameter of 70 mm having a storing device in the lower part thereof. In the apparatus, a liquid in the storing device is transported to the upper part of the metal tube by a circulating pump, and the liquid can flow on the wall face inside the tube like a falling film. The surface of the tube is constructed with a double jacket, which is controlled by a thermostat so as to be a constant temperature. One-time dynamic crystallization was carried out in the following procedure.

(1) Crystallization: the acrylic acid solution was supplied to the storing device and was made to flow on the wall face inside the tube like a falling film by using the circulating pump, and then the temperature of the jacket was decreased to the freezing point or lower to thereby crystallize about 60 to 90 mass % of the acrylic acid on the wall.

(2) Sweating: the circulating pump was stopped, and the temperature of the jacket was increased to near the freezing point to sweat about 2 to 20% of the acrylic acid. After sweating, the remaining liquid was pumped out.

(3) Melting: the temperature of the jacket was increased to the freezing point or higher to melt the crystal. The liquid was pumped out.

In the above operations, temperatures and freezing points were depended on the respective steps performed.

Thus, purified acrylic acid having a purity of 99.93 mass % was obtained. In this case, the contents of components other than the purified acrylic acid were 100 mass ppm of water, 475 mass ppm of acetic acid, 2 mass ppm of maleic acid, 30 mass ppm of acrylic acid dimmer, and 0.4 mass ppm of aldehydes.

Methoquinone was added as a stabilizer to the purified acrylic acid in a concentration of 200 mass ppm, and the temperature of the purified acrylic acid was adjusted to 25° C. by using a heat exchanger. Then, the purified acrylic acid was supplied to a storage tank through a line in which a cartridge filter made of polypropylene with a pore diameter of 1 μm was placed. Hereinafter, the filter is referred to as Filter C. The purified acrylic acid was continuously taken out of the storage tank in such a way that the residence time of the purified acrylic acid in the storage tank was three hours. Then, the purified acrylic acid was supplied to a product tank. At this time, the linear velocity of the acrylic acid solution in a Filter C portion was 0.01 m/s.

In a line through which the purified acrylic acid was taken out of the storage tank, a cartridge filter made of polypropylene with a pore diameter of 1 μm was placed. Hereinafter, the filter is referred to as Filter D. The operation was continuously performed for one month. However, the increase of pressure drop was not seen at Filter D, and a deposit such as polymer was also not seen on the surface of Filter D taken out. The increase of pressure drop was not seen also on Filter C; however, deposited polymer was on the surface of Filter C taken out.

This polymer was capable of being removed by cleaning with water and then with 10 mass % of an aqueous sodium hydroxide solution and further with water.

Comparative Example 3

An operation similar to Example 2 was carried out except that Filter C was not placed. After a continuous operation was carried out for 4 days, the increase of pressure drop was caused at Filter D, so that it was difficult to take the purified acrylic acid out of the storage tank. A deposited polymer was on the surface of Filter D taken out, and most of the filter pores were clogged.

Comparative Example 4

An operation similar to Example 2 was carried out except that Filter E with a pore diameter of 1 μm was placed in a line through which the acrylic acid solution was supplied to the crystallizing apparatus and that Filter C was not placed. After a continuous operation was carried out for 7 days, the increase of pressure drop was caused at Filter D, so that it was difficult to take the purified acrylic acid out of the storage tank. A deposited polymer was on the surface of Filter D taken out, and most of the filter pores were clogged.

Reference Example 2

Preparation of Crude Acrylic Acid

By a similar method to the case of Example 1 of Japanese Unexamined Patent Publication No. 2001-199931, an azeotropic distillation mixture was obtained from a column bottom of an azeotropic distillation column. The method comprised a vapor-phase catalytic oxidation reaction of propylene, absorption of the reaction gas by use of water as a absorbing solvent, stripping process of the aqueous acrylic acid solution obtained, and azeotropic distillation by use of toluene as an azeotropic solvent. The obtained mixture contained 96.9 mass % of acrylic acid, 0.06 mass % of acetic acid, 0.03 mass % of water, and 0.4 mass % of aldehydes.

Then, the azeotropic distillation mixture was supplied to a distillation column. The distillation column includes a sieve tray having a number of stages of 50 and a stage space of 147 mm; the upper portion of the overhead is provided with a distilling tube and a refluxing tube; the column side is provided with a raw material supplying tube; the column bottom is provided with a tube for extracting column bottom flow. The distillation was carried out at an overhead pressure of 35 hPa in a reflux ratio of 1.0 at a column bottom temperature of 92° C. At a time of distillation, a stabilizer was added to a reflux liquid, and the distillation was carried out while blowing oxygen into the column bottom flow. The distillation provided crude acrylic acid containing 99.70 mass % of acrylic acid, 0.06 mass % of acetic acid, 0.03 mass % of water, and 0.1 mass % of aldehydes from the overhead.

Example 3

To the crude acrylic acid obtained in Reference Example 2, 400 mass ppm of hydrazine hydrate, that is hydrazine one hydrate, as an aldehyde treating agent based on the amount of the crude acrylic acid was added. The resulting liquid was directly supplied to a column bottom of a purifying column without passing through a storage tank. The purifying column includes a sieve tray having a number of stages of 5 and a stage space of 147 mm; the upper portion of the overhead is provided with a distilling tube and a refluxing tube; the column bottom is provided with a raw material supplying tube and a tube for extracting column bottom flow. The distillation was continuously carried out at an overhead pressure of 55 hPa in a reflux ratio of 0.5.

To a reflux liquid, 250 mass ppm of methoquinone based on the amount of the crude acrylic acid was added as a polymerization inhibitor. The distillation was carried out while blowing oxygen into the column bottoms. The distillation provided purified acrylic acid having a purity of 99.89 mass % from the upper portion of the purifying column. In this case, the contents of components other than the purified acrylic acid were 400 mass ppm of water, 620 mass ppm of acetic acid, 0.04 mass ppm of aldehydes, and 70 mass ppm of methoquinone.

The purified acrylic acid was adjusted to 30° C. by using a heat exchanger, and then supplied to a storage tank through a line in which a cartridge filter made of polypropylene with a pore diameter of 1 μm was placed. Hereinafter, the filter is referred to as Filter F. The purified acrylic acid was continuously taken out of the storage tank in such a way that the residence time of the purified acrylic acid in the storage tank was 5 hours. Then, the purified acrylic acid was supplied to a product tank. At this time, the linear velocity of the purified acrylic acid in a Filter F portion was 0.01 m/s.

In a line through which the purified acrylic acid was taken out of the storage tank, a cartridge filter made of polypropylene with a pore diameter of 1 μm was placed. Hereinafter, the filter is referred to as Filter G. The extracting operation was continuously carried out for one month. However, the increase of pressure drop was not seen at Filter G, and a deposit such as polymer was also not seen on the surface of Filter G taken out. The increase of pressure drop was not seen also on Filter F; however, deposited polymer was on the surface of Filter F taken out. This polymer was capable of being removed by cleaning with water and then with 10 mass % of an aqueous sodium hydroxide solution and further with water.

Comparative Example 5

A similar operation to Example 3 was carried out except that Filter F was not placed. After a continuous operation was carried out for 2 weeks, the increase of pressure drop was caused at Filter G, so that it was difficult to take the purified acrylic acid out of the storage tank. A deposited polymer was on the surface of Filter G taken out, and most of the filter pores were clogged.

INDUSTRIAL APPLICABILITY

The present invention is practicable by placing a filter in existing facilities and easily applicable to a current method for producing acrylic acid.

The invention claimed is:

1. A method for producing acrylic acid, comprising steps of:
   purifying acrylic acid by crystallization, and
   storing the purified acrylic acid in a storage tank, wherein a process liquid containing 50 mass % or more of the purified acrylic acid is subjected to at least one filtering operation at 15 to 70° C. when the process liquid is supplied to the storage tank after purification.

2. The method of producing acrylic acid of claim 1, further comprising the steps of:
   (a) obtaining an acrylic acid-containing gas by a vapor-phase catalytic oxidation reaction from an acrylic acid raw material; and
   (b) obtaining a crude acrylic acid by at least one of absorbing or condensing the acrylic acid-containing gas.

3. The method of producing acrylic acid of claim 2, wherein the crude acrylic acid is obtained as a column bottom flow of an absorption column.

4. The method of producing acrylic acid of claim 1, wherein water is contained in acrylic acid supplied to the crystallization step in an amount of 0.5 mass % or more.

5. The method of producing acrylic acid of claim 1, wherein water is contained in acrylic acid after the crystallization step in an amount of 0.3 mass % or less.

* * * * *